(12) United States Patent
Franke et al.

(10) Patent No.: US 11,839,750 B2
(45) Date of Patent: Dec. 12, 2023

(54) INJECTION DEVICE

(71) Applicant: Sanofi, Paris (FR)

(72) Inventors: Beate Franke, Frankfurt am Main (DE); Ulrich Brueggemann, Bridgewater, NJ (US); Matthias Rau, Russelsheim (DE); Jeff Kablik, Bridgewater, NJ (US)

(73) Assignee: Sanofi, Paris (FR)

( * ) Notice: Subject to any disclaimer, the term of this patent is extended or adjusted under 35 U.S.C. 154(b) by 131 days.

(21) Appl. No.: 16/768,288

(22) PCT Filed: Nov. 30, 2018

(86) PCT No.: PCT/EP2018/083182
§ 371 (c)(1),
(2) Date: May 29, 2020

(87) PCT Pub. No.: WO2019/106165
PCT Pub. Date: Jun. 6, 2019

(65) Prior Publication Data
US 2021/0178082 A1 Jun. 17, 2021

(30) Foreign Application Priority Data
Dec. 1, 2017 (EP) .................................... 17306676

(51) Int. Cl.
*A61M 5/32* (2006.01)
*A61M 5/20* (2006.01)
(Continued)

(52) U.S. Cl.
CPC .......... *A61M 5/326* (2013.01); *A61M 5/2033* (2013.01); *A61M 5/288* (2013.01); *A61M 5/31501* (2013.01); *A61M 2005/3247* (2013.01)

(58) Field of Classification Search
CPC .... A61M 5/326; A61M 5/288; A61M 5/2033; A61M 5/31501; A61M 5/3293;
(Continued)

(56) References Cited

U.S. PATENT DOCUMENTS 3,780,734 A  12/1973 Wulff
5,609,577 A   3/1997 Haber et al.
(Continued)

FOREIGN PATENT DOCUMENTS

CN  1323230   11/2001
CN  102905743   1/2013
(Continued)

OTHER PUBLICATIONS

PCT International Preliminary Report on Patentability in International Appln. No. PCT/EP2018/083182, dated Jun. 2, 2020, 10 pages.
(Continued)

*Primary Examiner* — James D Ponton
*Assistant Examiner* — Neeraja Gollamudi
(74) *Attorney, Agent, or Firm* — Fish & Richardson P.C.

(57) ABSTRACT

The present invention relates to an injection device that includes a housing having an axis, and a needle sleeve that is axially movably within the housing. Axial movement of the needle sleeve into the housing is configured to actuate an injection process. The needle sleeve includes a first part that is slidably mounted to the housing, and a second part that protrudes from the housing and is rotationally coupled to the first part. The needle sleeve includes a locking mechanism that is configured to prevent axial movement of the needle sleeve into the housing until the second part of the needle sleeve has been rotated relative to the first part of the needle sleeve.

24 Claims, 8 Drawing Sheets

(51) Int. Cl.
*A61M 5/28* (2006.01)
*A61M 5/315* (2006.01)

(58) Field of Classification Search
CPC .............. A61M 5/2466; A61M 5/3243; A61M 5/3271; A61M 5/20; A61M 2005/3247; A61M 2005/2013; A61M 2005/2474; A61M 2005/247; A61M 5/3257; A61M 5/3234; A61M 5/3273; A61M 5/3221; A61M 2005/3263; A61M 2005/3267; A61M 2005/3289; A61M 2005/206; A61M 2005/2073; A61M 2005/208
See application file for complete search history.

(56) References Cited

U.S. PATENT DOCUMENTS

| | | |
|---|---|---|
| 2004/0102740 A1 | 5/2004 | Meloul |
| 2008/0147006 A1 | 6/2008 | Bninnberg et al. |
| 2008/0177235 A1* | 7/2008 | DiBiasi ................ A61M 5/326 604/192 |
| 2010/0262083 A1 | 10/2010 | Grunhut et al. |
| 2012/0265136 A1* | 10/2012 | Lawlis ................ A61M 5/3156 604/110 |
| 2012/0316508 A1 | 12/2012 | Kirchhofer |
| 2013/0110050 A1 | 5/2013 | Boyd et al. |
| 2013/0324934 A1* | 12/2013 | Holmqvist .......... A61M 5/2033 604/192 |
| 2014/0323976 A1 | 10/2014 | Jugl et al. |
| 2015/0367072 A1 | 12/2015 | Constantineau et al. |
| 2015/0367073 A1* | 12/2015 | Standley ................ A61M 5/321 604/91 |
| 2018/0117240 A1 | 5/2018 | Archilla et al. |

FOREIGN PATENT DOCUMENTS

| | | |
|---|---|---|
| CN | 102917738 | 2/2013 |
| CN | 103957970 | 7/2014 |
| CN | 104968381 | 10/2015 |
| EP | 1949928 | 7/2008 |
| JP | 2002-522171 | 7/2002 |
| JP | 2008-246190 | 10/2008 |
| JP | 2013-523198 | 6/2013 |
| JP | 2017-525469 | 9/2017 |
| WO | WO 00/09186 | 2/2000 |
| WO | WO 2011/117284 | 9/2011 |
| WO | WO 2011/123024 | 10/2011 |
| WO | WO 2013/050479 | 4/2013 |
| WO | WO 2014/095424 | 6/2014 |
| WO | WO 2015/185664 | 12/2015 |
| WO | WO 2017/089277 | 6/2017 |

OTHER PUBLICATIONS

PCT International Search Report and Written Opinion in International Appln. No. PCT/EP2018/083182, dated Feb. 12, 2019, 14 pages.

* cited by examiner

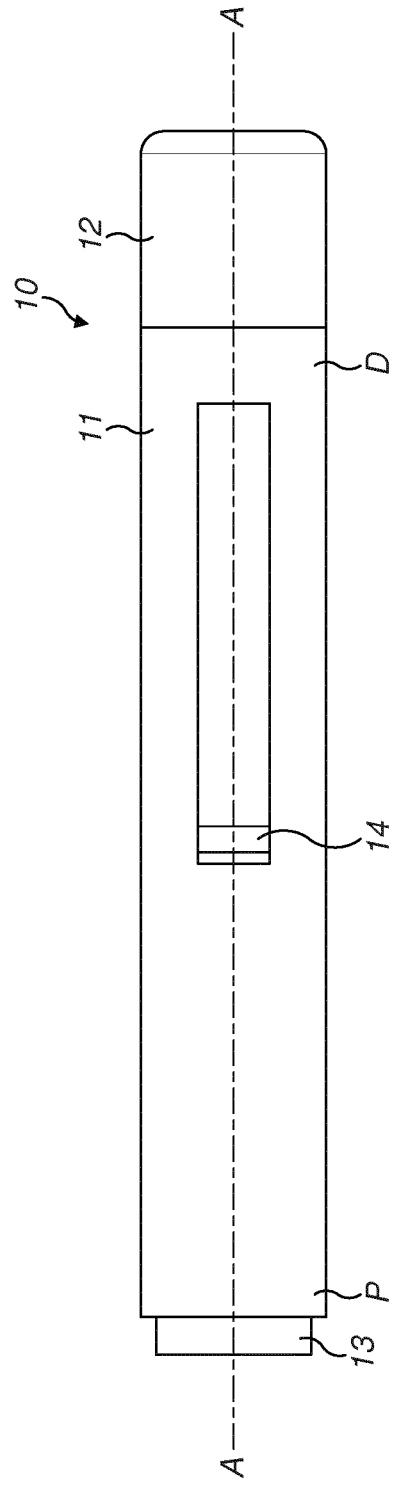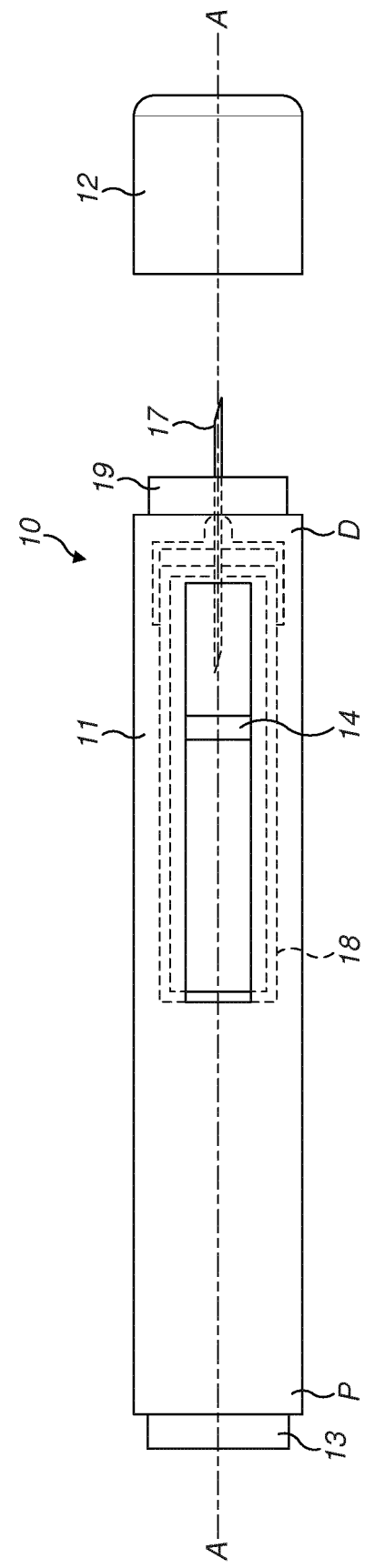
FIG. 1A
FIG. 1B

INJECTION DEVICE

CROSS REFERENCE TO RELATED APPLICATIONS

The present application is the national stage entry of International Patent Application No. PCT/EP2018/083182, filed on Nov. 30, 2018, and claims priority to Application No. EP 17306676.2, filed on Dec. 1, 2017, the disclosures of which are incorporated herein by reference.

TECHNICAL FIELD

The present disclosure relates to an injection device for a medicament.

BACKGROUND

Cartridge injection devices, for example cartridge autoinjectors, typically have a sealed cartridge that contains a medicament and a needle that is initially separated from the cartridge. Before use of the injection device the cartridge and needle are combined so that the needle pierces the cartridge. A plunger can then be moved into the cartridge to dispense medicament through the needle for injection into the tissue of a user.

SUMMARY

According to an aspect of the disclosure, an injection device includes: a housing having an axis, and a needle sleeve that is axially movably within the housing, wherein axial movement of the needle sleeve into the housing is configured to actuate an injection process. The needle sleeve comprises: a first part slidably mounted to the housing, a second part that protrudes from the housing and is rotatably coupled to the first part such that the second part can be rotated relative to the first part about the axis, and a locking mechanism arranged to prevent axial movement of the needle sleeve into the housing until the second part of the needle sleeve has been rotated relative to the first part of the needle sleeve.

The locking mechanism may comprise a slot and an engaging member, wherein the engaging member may be disposed in the slot, and wherein the slot may be arranged to prevent axial movement of the needle sleeve until the second part of the needle sleeve has been rotated relative to the first part about the axis.

The second part of the needle sleeve may comprise one of the slot and the engaging member, and the housing may comprise the other of the slot and the engaging member.

The slot may comprise a radially extending portion and an axially extending portion, and rotation of the needle sleeve relative to the first part may move the engaging member from the radially extending portion into the axially extending portion such that the needle sleeve can move axially into the housing.

The second part of the needle sleeve may be rotatable between a first position in which the locking mechanism prevents the needle sleeve from moving axially into the housing, and a second position in which the locking mechanism permits the needle sleeve to move axially into the housing.

The injection device may further comprise a reservoir for a medicament and a spring-loaded mechanism for dispensing medicament from the reservoir, and further comprising a catch arranged to hold the spring-loaded mechanism before use of the injection device, and wherein movement of the needle sleeve into the housing may release the catch to actuate the injection process.

In some examples, the locking mechanism comprises a slot and a protrusion, and wherein rotation of the second part of the needle sleeve brings the slot and the protrusion into alignment to permit axial movement of the needle sleeve into the housing.

The slot may be formed in one of the housing and the second part of the needle sleeve, and the protrusion may be formed in the other of the housing and the second part of the needle sleeve. In one example, the slot is formed in the housing and the protrusion is formed on the second part of the needle sleeve. In another example, the slot is formed in the second part of the needle sleeve and the protrusion is formed on the housing.

The protrusion may be adapted to snap into the slot when the slot and protrusion are aligned with each other to prevent further rotation of the needle sleeve. The snap may also create a sound to inform the user that the rotation is complete.

The second part of the needle sleeve may comprise a circumferentially extending slot, and the first part of the needle sleeve may comprise a catch that engages the circumferentially extending slot to couple the second part to the first part and permit rotational movement of the second part relative to the second part as the catch moves within the circumferentially extending slot.

In some examples, the injection device may further comprise a member arranged to prevent rotation of the first part of the needle sleeve relative to the housing. For example, the member may extend from the housing and engage an axially extending slot or groove in the first part of the needle sleeve, or the member may extend from the first part of the needle sleeve and engage an axially extending slot in the housing.

In various examples, one of the first part of the needle sleeve and the housing comprises an axially extending slot, and the other of the first part of the needle sleeve and the housing comprises a protrusion that engages the axially extending slot to prevent rotation of the first part of the needle sleeve relative to the housing.

The second part of the needle sleeve may comprise an axially extending slot or a protrusion, and wherein the axially extending slot or the protrusion of the second part may be aligned with the protrusion or axially extending slot, respectively, of the housing after the second part of the needle sleeve has been rotated. In this way, the axially extending slot and protrusion that allows the first part of the needle sleeve to move axially and prevents rotation of the first part of the needle sleeve also serves to prevent axial movement of the second part of the needle sleeve (and therefore the entire needle sleeve) until the second part of the needle sleeve has been rotated.

The injection device may further comprise a needle unit having a needle, and a cartridge having a reservoir for a medicament. Prior to use of the injection device the reservoir may be sealed from the needle, and rotation of the second part of the needle sleeve may be configured to move the needle unit such that the needle is placed in fluid communication with the reservoir.

Therefore, actuation of the injection process by axial movement of the needle sleeve is prevented at least until the second part of the needle sleeve has been rotated to engage the needle unit and cartridge.

The second part of the needle sleeve may comprise an engaging member arranged to move the needle unit in an axial direction when the second part of the needle sleeve is rotated.

In some examples, the engaging member may comprise a helical guide arranged to engage a protrusion on the needle unit and move the needle unit as the second part of the needle sleeve is rotated.

The engaging member may be arranged to disengage from the needle unit after the second part has been rotated. In this way, the needle sleeve is decoupled from the needle unit and is able to move axially independently of the needle unit to actuate the injection process.

The injection device may further comprise a piston disposed in the cartridge and a piston drive mechanism arranged to drive the piston to dispense medicament via the needle. Axial movement of the needle sleeve into the housing may be adapted to actuate the piston drive mechanism.

The cartridge may comprise a medicament in the reservoir.

According to another aspect of the disclosure, a method of using an injection device that includes a housing and a needle sleeve is provided. The method includes: rotating a part of the needle sleeve relative to the housing to unlock the needle sleeve, and moving the needle sleeve into the housing to actuate an injection process.

These and other aspects of the disclosure will be apparent from and elucidated with reference to the embodiments described hereinafter.

BRIEF DESCRIPTION OF THE FIGURES

Embodiments of the invention are described, by way of example only, with reference to the accompanying drawings, in which:

FIG. 1A is a schematic side view of an injection device that embodies the invention, and a removable cap;

FIG. 1B is a schematic side view of the injection device of FIG. 1A, with the cap removed from the housing;

DETAILED DESCRIPTION

Figure 2:
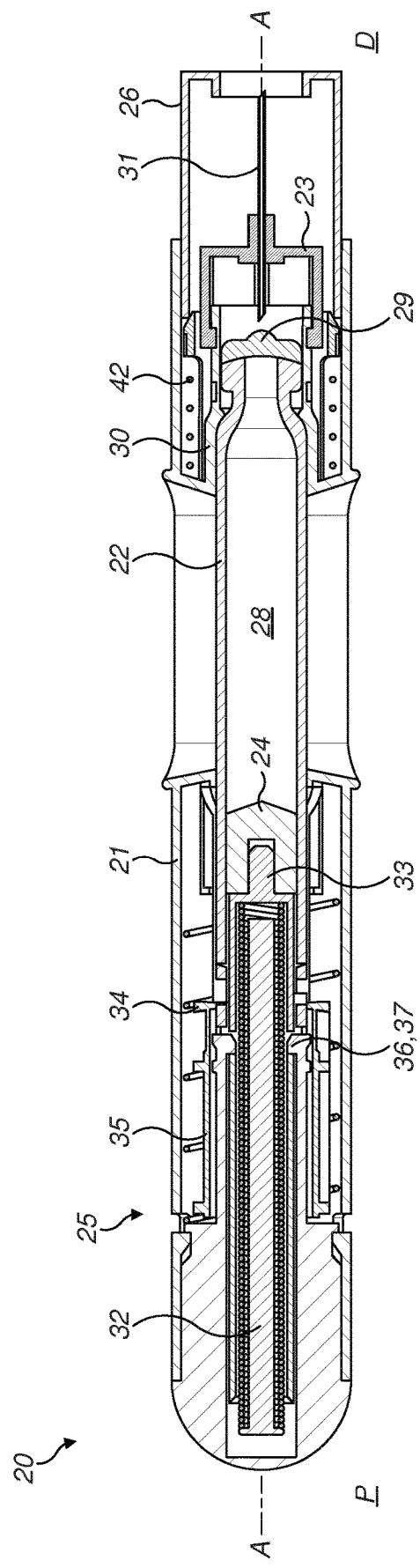
FIG. 2 is a cross-sectional view of an injection device.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include for example, mechanical, pneumatic, chemical, or electrical energy. Mechanical energy sources can include for example springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause an injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an example of a drug delivery device 10 is shown in FIGS. 1A and 1B. Device 10, as described above, is configured to inject a medicament into a patient's body. Device 10 includes a housing 11 which typically contains a cartridge that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixed relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A and 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the cartridge 18 within housing 11 is moved in a proximal direction relative to housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between needle 17 and housing 11 can be locked with a locking mechanism. In addition, button 13 or other components of device 10 can be locked as required.

FIG. 2 illustrates an example injection device 20 having a housing 21, a cartridge 22, a needle unit 23, and a needle sleeve 26. The injection device 20 further includes a piston 24 and a piston drive mechanism 25.

The cartridge 22 defines a reservoir 28 that contains a medicament and is mounted within the housing 21. A distal end D of the cartridge 22 is sealed by an end cap 29. A cartridge mounting portion 30 of the housing 21 supports the cartridge 22. As illustrated, a part of the cartridge mounting portion 30 is tubular and surrounds the distal end of the cartridge 22. This tubular part of the cartridge mounting portion 30 has an external surface disposed within the housing 21.

As shown in FIG. 2, in an initial condition the proximal end of needle 31 of the needle unit 23 is spaced from the end cap 29 at the distal end of the cartridge 22. Before or during use of the injection device 20 the needle unit 23 is moved into engagement with the distal end of the cartridge 22 such that the proximal end of needle 31 pierces the end cap 29 of the cartridge 22. In this way, medicament can be expelled from the reservoir 28 via the needle 31, as explained further hereinafter.

In the initial condition, illustrated in FIG. 2, the piston 24 is positioned at a proximal end of the reservoir 28 in the cartridge 22, and the piston drive mechanism 25 is disposed in the proximal end of the housing 21. The piston drive mechanism 25 comprises a spring 32, a plunger 33, and a catch 34. The spring 32 is arranged to urge the plunger 33 against the piston 24 and into the reservoir 28 to expel medicament from the reservoir 28 during use. In the initial condition before use, as illustrated, the spring 32 is held in a compressed state by a catch 34. Specifically, the catch 34 holds the plunger 33, which holds the spring 32 in a compressed state such that no force is applied to the piston 24. In this state, the piston drive mechanism 25 is pre-loaded.

As explained further hereinafter, the injection device 20 is actuated by an actuator, in this example the needle sleeve 26 that is rotationally and slidably movable within the housing 21 and protrudes from the distal end of the housing 21. In this way, during use, the needle sleeve 26 is placed against the user's skin and the injection device 20 is pushed towards the user's skin while holding the housing 21, this moves the needle sleeve 26 in a proximal direction, into the housing 21.

The needle sleeve 26 acts to release the catch 34 once the needle sleeve 26 has moved into the housing 21 in a proximal direction. Once the catch 34 is released, the spring 32 urges the plunger 33 against the piston 24 and into the reservoir 28.

As illustrated in FIG. 2, the catch 34 may include a tubular element 35 that surrounds the plunger 33 and spring 32. The tubular element 35 includes protrusions 36 that engage recesses 37 in the plunger 33, such that in the position illustrated in FIG. 2 the plunger 33 is prevented from moving in a distal direction by the protrusions 36 and the recesses 37.

As the needle sleeve 26 is moved proximally into the housing 21, an end of the needle sleeve 26 engages the tubular element 35, causing the tubular element 35 to rotate about the axis A of the injection device 20. This rotation causes the protrusions 36 to disengage from the recesses 37, thereby releasing the plunger 33, which then moves under the force of the spring 32 into the reservoir 28.

In one example, the end of the needle sleeve 26 that engages the tubular element 35 may comprise a chamfer (i.e. angled edge) that engages a protrusion on the tubular element 35 to cause the rotation. In other examples, the tubular element 35 may comprise a chamfer (i.e. angled edge) that is engaged by a protrusion on the needle sleeve 26 to cause the rotation.

In other examples, the catch 34 may comprise arms that include the protrusions that engage the plunger 33. In this case, the needle sleeve 26 might deflect the arms by lifting them to disengage the protrusions from the recesses, thereby releasing the plunger 33.

A biasing member, for example a spring 42, may be arranged to act between the housing 21 and the needle sleeve 26 to urge the needle sleeve 26 in a distal direction so that it protrudes from the distal end of the housing 21.

In other examples, movement of the needle sleeve 26 into the housing 21 can actuate the injection process in other ways. For example, movement of the needle sleeve 26 into the housing 21 may move an intermediate component to release the catch 34. In other examples, movement of the needle sleeve 26 into the housing 21 may close or open an electronic switch which in turn releases the plunger 33. In still more examples, the plunger 33 may be electronically or pneumatically actuated by an actuator during the injection process, and in such examples movement of the needle sleeve 26 into the housing 21 may activate such an actuator. Therefore, it will be appreciated that movement of the needle sleeve 26 into the housing 21 can actuate the injection process (i.e. movement of the plunger 33 into the reservoir 28) in various ways.

Before or during use, the needle unit 23 is combined with the cartridge 22 before the catch 34 is released. As explained below, rotating a part of the needle sleeve 26 about the axis A causes one of the needle unit 23 or the cartridge 22 to move axially within the housing 21 so that the needle 31 is placed in fluid communication with the reservoir 28. A subsequent movement of the needle sleeve 26 in a proximal direction releases the catch 34 so that plunger 33 begins delivery of the medicament via the needle 31. In various examples described hereinafter, a part of the needle sleeve 26 must be rotated to engage the needle unit 23 and cartridge 22 before the needle sleeve 26 can move axially into the housing 21 to actuate the piston drive mechanism 25.

Figure 3:
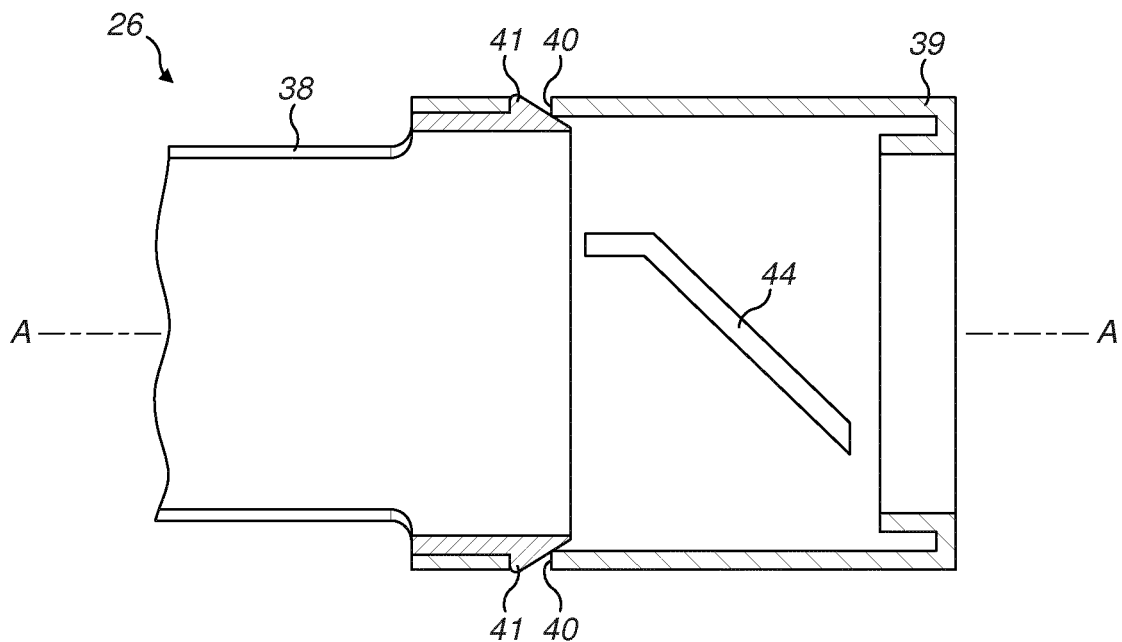
FIG. 3 is a cross-sectional view of a needle sleeve.

FIG. 3 illustrates the distal end of the needle sleeve 26 of the injection device 20. As shown, the needle sleeve 26 has a first part 38 and a second part 39. The second part 39 of the needle sleeve 26 is rotationally coupled to the end of the first part 38. As shown, the second part 39 includes a slot 40 and the first part 38 includes a catch 41 that is received in the slot 40.

In the example of FIG. 3, the slot 40 is only slightly larger than the catch 41. In an initial position, the catch 41 is not aligned with the slot 40 and is in a deflected state acting against the inside of the second part 39 of the needle sleeve 36. Rotation of the second part 39 of the needle sleeve 26 about the axis A moves the catch 41 into alignment with the slot 40 so that the catch 41 snaps into the slot 40 to prevent further rotation.

Figure 4:
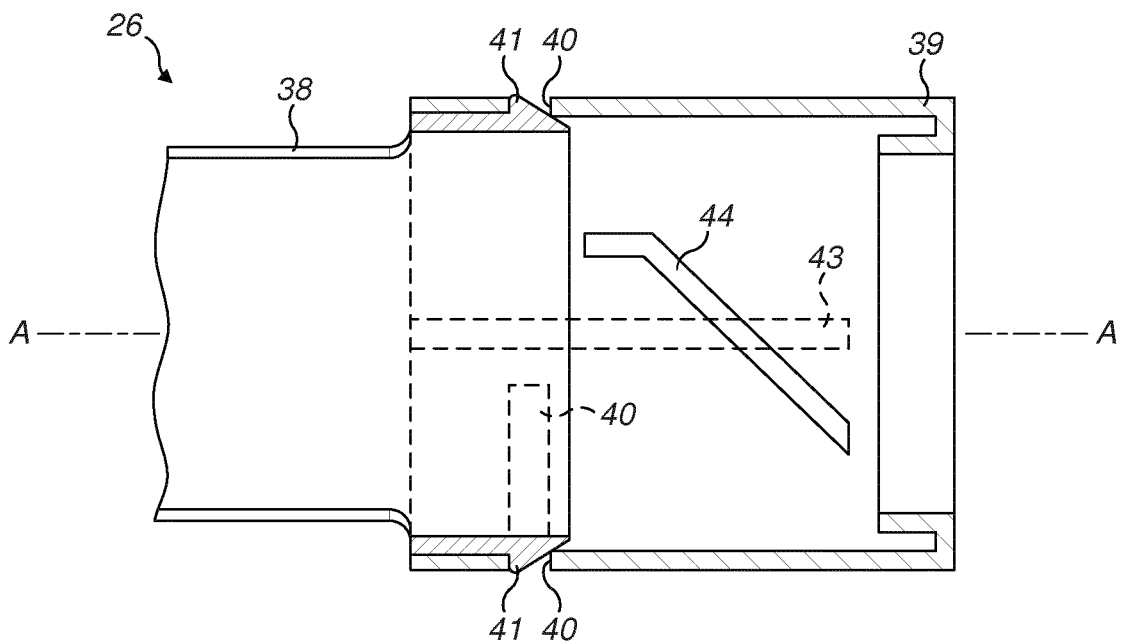
FIG. 4 is a cross-sectional view of a needle sleeve.

In the example of FIG. 4, the slot 40 extends circumferentially about the needle sleeve 26. The slot 40 thereby allows the second part 39 to rotate relative to the first part 38 about axis A as the catch 41 moves within the slot 40. The extent of rotation is limited by the length of the slot 40. In an initial position the catch 41 is at a first end of the slot 40, and rotation of the second part 39 of the needle sleeve 26 moves the catch 41 to an opposite end of the slot 40.

In the examples of FIGS. 3 and 4, there are two slots 40 arranged on opposite sides of the needle sleeve 26. However, it will be appreciated that only one slot 40 may be provided, or more than two slots 40 may be provided, and the first part 39 will have a corresponding number of catches 41.

As also illustrated in FIG. 4, in some examples the second part 39 of the needle sleeve 26 includes an axially extending slot 43. The axially extending slot 43 moves as the second part 39 of the needle sleeve 26 is rotated. Rotation of the second part 39 of the needle sleeve 26 moves the axially extending slot 43 into alignment with a protrusion (not illustrated) on the housing. In this way, the axially extending slot 43 and protrusion act as a locking mechanism because the protrusion will prevent axial movement of the needle sleeve 26 into the housing 21 until the second part 39 of the needle sleeve 26 has been rotated to align the axially extending slot 43 with the protrusion.

Also shown in FIGS. 3 and 4, the second part 39 of the needle sleeve 26 also includes an engaging member, in this example a helical guide 44 arranged on an internal surface of the second part 39 of the needle sleeve 26, extending partially about the internal circumference of the needle sleeve 26. In examples, the needle sleeve 26 may comprise one or more helical guides 44, for example two helical guides 44, or three helical guides 44.

The helical guide 44 acts to move the needle unit 23 into engagement with the cartridge 22 as the second part 39 of the needle sleeve 26 is rotated.

Figure 5A:
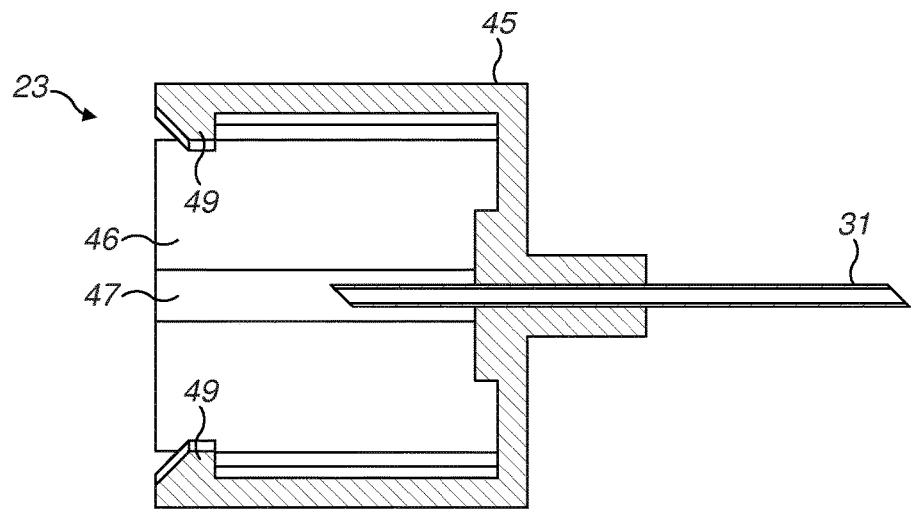
FIGS. 5A to 5C show a needle unit for use with the injection device.
Figure 5B:
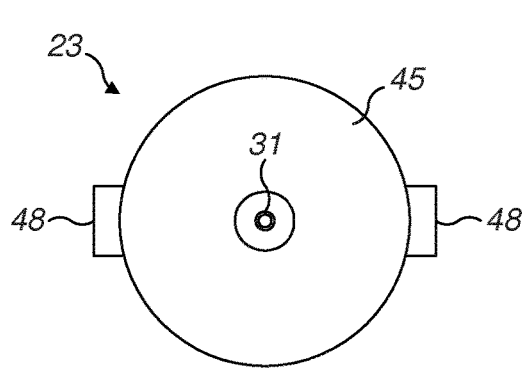
Figure 5C:
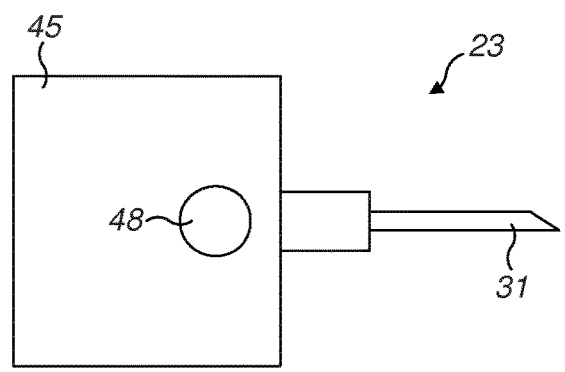

FIGS. 5A to 5C illustrate a needle unit 23 that may be used with the needle sleeve 26 described with reference to FIGS. 3 and 4. As shown in FIG. 5A, the needle unit 23 includes a needle body 45 to which a needle 31 is attached. The needle body 45 includes a recess 46. The recess 46 is adapted to be positioned over the cartridge mounting portion 30 (see FIG. 2) of the housing 21 (see FIG. 2) when the needle unit 23 is combined with the cartridge 22 (see FIG. 2) during use of the injection device 20.

As shown in FIG. 5A, and referring to FIG. 2, the needle body 45 includes a groove 47 arranged to cooperate with a rail (not illustrated) on the cartridge mounting portion 30 of the housing 21. The groove 47 is located on the internal surface of the needle body 45, in the recess 46. The cooperation of the rail and the groove 47 prevents rotation of the needle unit 23 relative to the housing 21 and cartridge 22, and guides the needle unit 23 in an axial direction when the helical guide 44 of the second part 39 of the needle sleeve 26 pushes the needle unit 23 onto the cartridge 22, as explained hereinafter.

As shown in FIGS. 5B and 5C, the outer surface of the needle body 45 includes protrusions 48. In this example, the external surface of the needle body 45 includes two protrusions 48, but it will be appreciated that one protrusion 48 is provided for each helical guide 44 on the second part 39 of the needle sleeve 37. The protrusions 48 are generally circular, but may be other shapes. The protrusions 48 are equally spaced around the circumference of the needle body 45.

Referring to FIGS. 2 to 5C, the protrusions 48 on the needle body 45 are arranged to engage with the helical guides 44 on the second part 39 of the needle sleeve 26 such that rotation of the second part 39 of the needle sleeve 26 causes axial movement of the needle unit 23 towards the cartridge 22. In this way, during use of the injection device 20, the user rotates the second part 39 of the needle sleeve 26 to engage the needle unit 23 with the cartridge 22 and place the needle 31 in fluid communication with the reservoir 28 before the injection process is started.

Figure 6A:
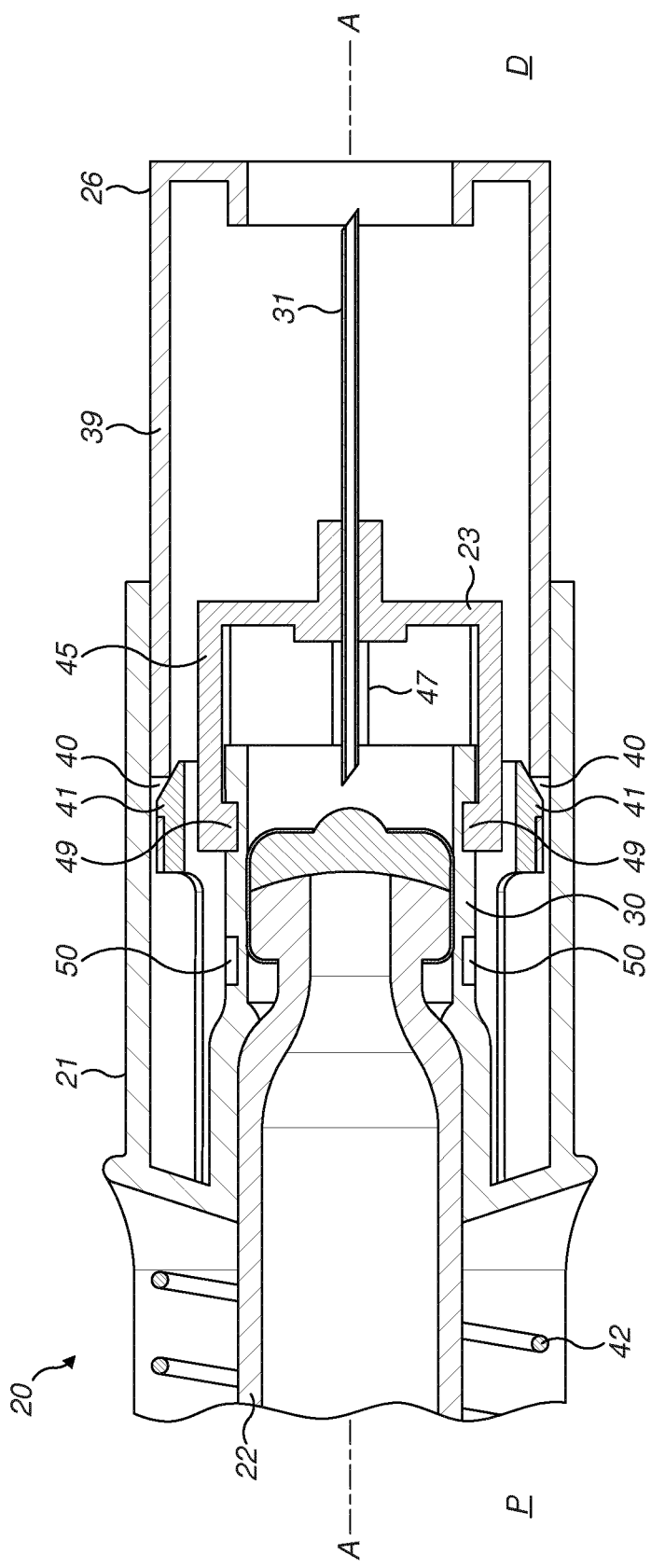
FIGS. 6A to 6C show steps of operation of the injection device.
Figure 6B:
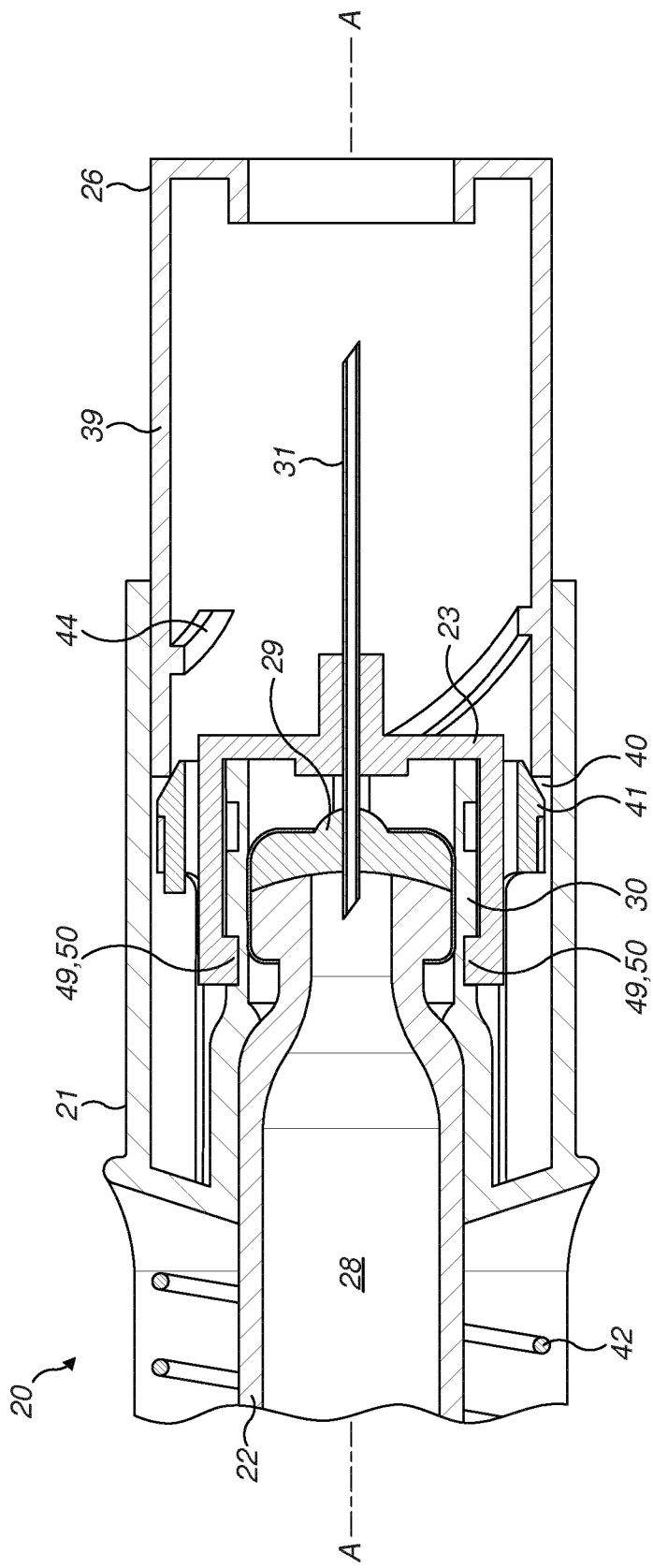
Figure 6C:
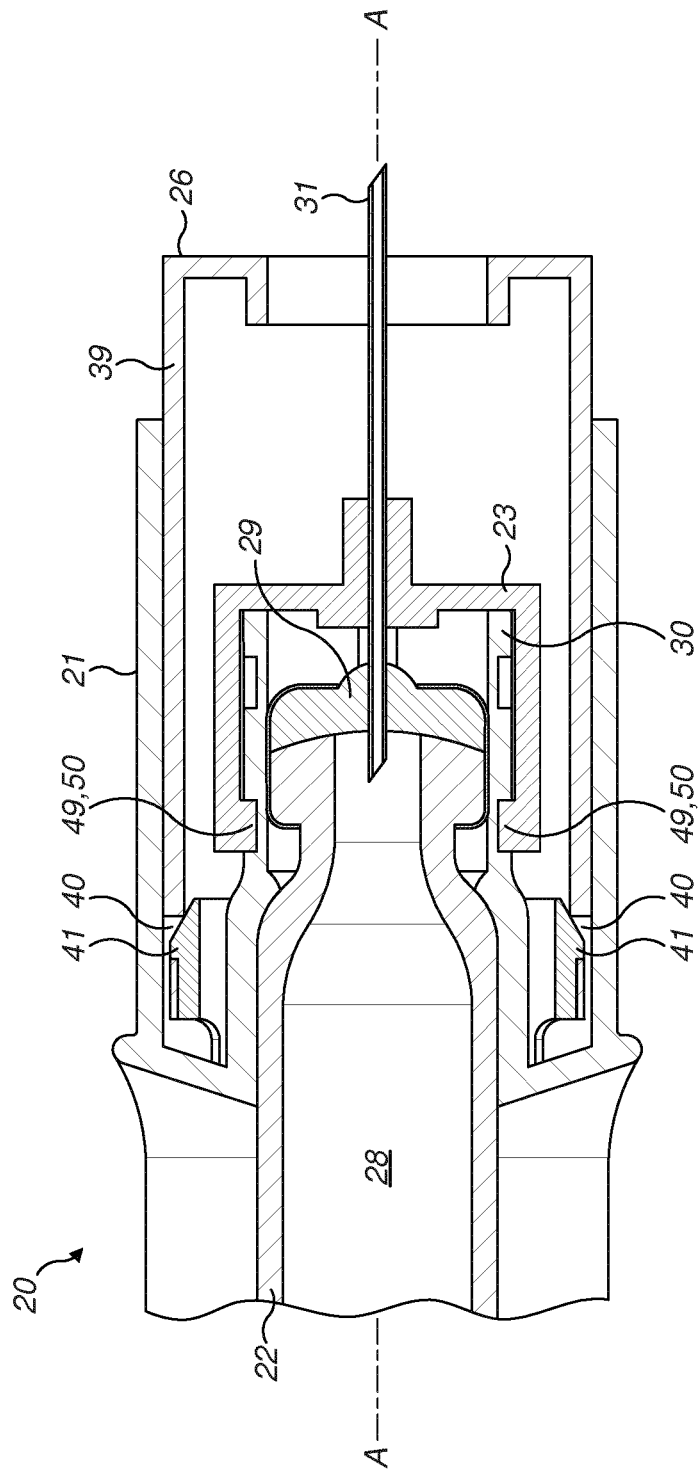

FIGS. 6A to 6C illustrate the process of combining of the needle unit 23 and cartridge 22.

As shown in FIG. 6A, and referring also to FIGS. 3 to 5C, in this initial position the needle unit 23 is spaced from the cartridge 22. The needle sleeve 26 is in an extended position and covers the needle 31. In particular, the second part 39 of the needle sleeve 26 protrudes from a distal end of the housing 21. In this position, the needle unit 23 is held in place by a combination of the engagement between the protrusions 48 and helical guides 44, the engagement between a proximal end of the needle body 45 and the cartridge mounting portion 30 of the housing 21, and engagement between the rail (not illustrated) and groove 47.

As the second part 39 of the needle sleeve 26 is rotated the engagement between the helical guides 44 on the second part 39 of the needle sleeve 26 and the protrusions 48 on the needle unit 23 drive the needle unit 23 in an axial direction towards the cartridge 22. The rail and groove 47 prevent rotation of the needle unit 23 and guide the needle unit 23 onto the cartridge mounting portion 30.

As shown in FIG. 6A, the proximal end of the needle body 45 includes catches 49 that initially have to be deflected to allow the needle body 45 to move over the cartridge mounting portion 30 of the housing 21. In the initial position, shown in FIG. 6A, engagement between the catches 49 and the cartridge mounting portion 30 help to hold the needle unit 23 in position within the injection device 20.

FIG. 6B shows the injection device 20 after the second part 39 of the needle sleeve 26 has been rotated to move the needle unit 23 into engagement with the cartridge 22. As shown, the catches 49 on the proximal end of the needle body 45 have engaged with recesses 50 on the cartridge mounting portion 30, so that the needle unit 23 is secured in place on the cartridge mounting portion 30. Also, a proximal end of the needle 31 has pierced the end cap 29 of the cartridge 22, so that the needle 31 is in fluid communication with the reservoir 28. The needle sleeve 26 remains in an extended position due to the action of the spring 42.

Due to the rotation of the second part 39 of the needle sleeve 26 the helical members 44 have disengaged from the protrusions (48, see FIGS. 5A to 5C), so that the needle sleeve 26 is able to move axially independently of the needle unit 23.

Furthermore, as explained previously with reference to FIGS. 3 to 5C, rotation of the second part 39 of the needle sleeve 26 moves the catches 41 into engagement with the slots 40 (FIG. 3), or moves the catches 41 along the slots 40 (FIG. 4). Rotation of the second part 39 of the needle sleeve 26 has also brought the axially extending slot 43 into line with the protrusion on the housing 21, so that the needle sleeve 26 is not able to move axially into the housing 21.

FIG. 6C shows the injection device 20 after the injection device 20 has been pressed against the user's skin to start the injection process. As illustrated, the needle sleeve 26 has moved proximally into the housing 21, exposing the needle 31 so that the needle 31 can pierce the user's skin. Also, as explained previously, proximal movement of the needle sleeve 26 into the housing 21 releases the catch (34, see FIG. 2) of the piston drive mechanism (25, see FIG. 2) to release the plunger (33, see FIG. 2), and the spring (32, see FIG. 2) then drives the piston (24, see FIG. 2) into the cartridge 22 to dispense medicament from the reservoir 28 via the needle 31.

After use, the spring 42 urges the needle sleeve 26 back to an extended position to re-cover the needle 31.

Figure 7A:
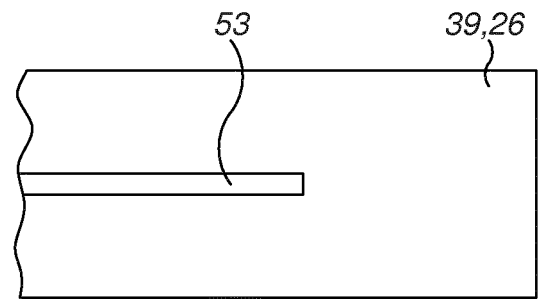
FIG. 7A shows an alternative needle sleeve for the injection device.
Figure 7B:
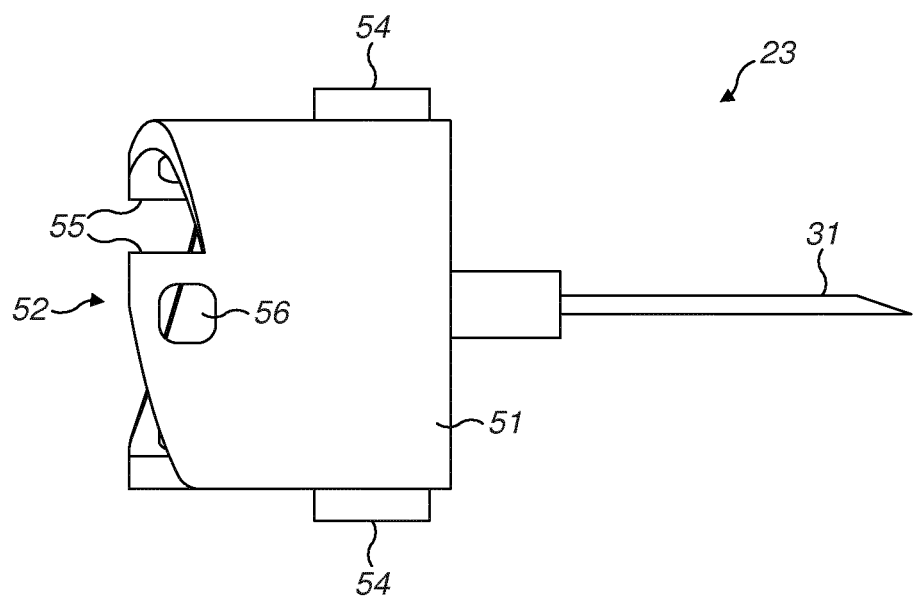
FIG. 7B shows an alternative needle unit for the injection device.

FIGS. 7A and 7B illustrate an alternative example injection device 20. In particular FIG. 7A illustrates an alternative second part 39 of the needle sleeve 26 and FIG. 7B illustrates the needle unit 23 for use with the alternative second part 39. The second part 39 of the needle sleeve 26 of FIG. 7A and needle unit 23 of FIG. 7B can be used with the injection device 20 of FIG. 2, but in this example, the needle unit 23 is rotationally mounted within the housing 21 and there is no rail and groove 47 as described with reference to previous examples.

Referring to FIGS. 2, 7A and 7B, the needle unit 23 has a needle body 51 having a recess 52, and an internal thread in the recess 52. The internal thread is arranged to engage with an external thread on the cartridge mounting portion 30 of the housing 21, or with an external thread on the cartridge 22. In an initial position the thread is aligned or partially started, such that on rotation of the needle unit 23 (explained below) the thread moves the needle unit 23 axially into engaged with the cartridge 22. In this way, the thread acts to guide the needle unit 23 into engagement with the cartridge 22 when the second part 39 of the needle sleeve 26 is rotated.

The internal surface of the needle sleeve 26 includes a groove 53, preferably two grooves 53. The external surface of the needle body 51 includes a protrusion 54, preferably two protrusions 54, that engage with the grooves 53 of the second part 39 of the needle sleeve 26. In this way, rotating the second part 39 of the needle sleeve 26 in the housing 21 causes rotation of the needle unit 23 within the housing 21, and the thread moves the needle unit 23 axially into engagement with the cartridge 22 so that the needle 31 is placed in fluid communication with the reservoir 28.

As shown in FIG. 7B, the needle unit 23 may also include end stops 55 that engage a part of the cartridge mounting portion 30 after the needle unit 23 has been rotated onto the cartridge mounting portion 30 by the thread. Additionally or alternatively, recesses 56 may be provided to engage with catches on the cartridge mounting portion 30, to secure the needle unit 23 on the cartridge mounting portion 30.

The threaded connection between the needle unit 23 and cartridge mounting portion 30 may have a high pitch, so that comparatively less rotation is needed to achieve the desired axial movement. For example, the rotation may be between 30 and 120 degrees, or about 90 degrees. However, the rotation may be greater than 120 degrees, for example 180 degrees.

In various examples, the threaded connection may comprise an external thread on the cartridge mounting portion 30 and an internal thread on the needle unit 23, or alternatively one of the internal and external threads may be replaced by a protrusion arranged to engage the other thread, so that on rotation of the needle sleeve 23 the protrusion follows the path of the thread and moves the needle unit 23 into engagement with the cartridge 22.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. An injection device comprising:
a housing having an axis; and
a needle sleeve that is axially movable within the housing, wherein an axial movement of the needle sleeve into the housing is configured to actuate an injection process,
wherein the needle sleeve comprises:
a first part slidably mounted to the housing,
a second part that protrudes from the housing and is rotatably coupled to the first part such that the second part can be rotated relative to the first part about the axis, wherein the second part is configured to be gripped by a user to rotate, and
a locking mechanism configured to prevent the axial movement of the needle sleeve into the housing until the second part of the needle sleeve has been rotated relative to the first part of the needle sleeve.

2. The injection device of claim 1, wherein the locking mechanism comprises a slot and an engaging member, wherein the engaging member is disposed in the slot, and wherein the slot is configured to prevent the axial movement of the needle sleeve until the second part of the needle sleeve has been rotated relative to the first part about the axis.

3. The injection device of claim 2, wherein the second part of the needle sleeve comprises one of the slot and the engaging member, and wherein the housing comprises the other of the slot and the engaging member.

4. The injection device of claim 2, wherein the slot comprises a radially extending portion and an axially extending portion, and wherein rotation of the second part of the needle sleeve relative to the first part of the needle sleeve moves the engaging member from the radially extending portion into the axially extending portion such that the needle sleeve can move axially into the housing.

5. The injection device of claim 1, wherein the second part of the needle sleeve is rotatable between a first position in which the locking mechanism prevents the needle sleeve from moving axially into the housing, and a second position in which the locking mechanism permits the needle sleeve to move axially into the housing.

6. The injection device of claim 1, further comprising:
a reservoir for a medicament and a spring-loaded mechanism for dispensing medicament from the reservoir, and
a catch configured to hold the spring-loaded mechanism before use of the injection device, wherein the catch is configured such that the axial movement of the needle sleeve into the housing releases the catch to actuate the injection process.

7. The injection device of claim 6, wherein the locking mechanism comprises a slot and a protrusion, and wherein rotation of the second part of the needle sleeve brings the slot and the protrusion into alignment to permit the axial movement of the needle sleeve into the housing.

8. The injection device of claim 7, wherein the slot is formed in one of the housing and the second part of the needle sleeve, and the protrusion is formed in the other of the housing and the second part of the needle sleeve.

9. The injection device of claim 7, wherein the protrusion is adapted to snap into the slot when the slot and the protrusion are aligned with each other to prevent a rotation of the needle sleeve.

10. The injection device of claim 9, wherein the second part of the needle sleeve comprises a circumferentially extending slot, and the first part of the needle sleeve comprises a catch that engages the circumferentially extending slot to couple the second part to the first part and permit a rotational movement of the second part relative to the first part as the catch moves within the circumferentially extending slot.

11. The injection device of claim 1, further comprising a member configured to prevent a rotation of the first part of the needle sleeve relative to the housing.

12. The injection device of claim 1, wherein one of the first part of the needle sleeve and the housing comprises an axially extending slot, and the other of the first part of the needle sleeve and the housing comprises a protrusion that engages the axially extending slot to prevent rotation of the first part of the needle sleeve relative to the housing.

13. The injection device of claim 12, wherein the second part of the needle sleeve comprises an axially extending slot or a protrusion, and wherein the axially extending slot or the protrusion of the second part is aligned with the protrusion or the axially extending slot, respectively, of the housing after the second part of the needle sleeve has been rotated.

14. The injection device of claim 1, further comprising a needle unit having a needle, and a cartridge having a reservoir for a medicament, wherein prior to use of the injection device the reservoir is sealed from the needle, and wherein rotation of the second part of the needle sleeve is configured to move the needle unit such that the needle is placed in fluid communication with the reservoir.

15. The injection device of claim 14, wherein the second part of the needle sleeve comprises an engaging member configured to move the needle unit in an axial direction when the second part of the needle sleeve is rotated.

16. The injection device of claim 15, wherein the engaging member comprises a helical guide configured to engage a protrusion on the needle unit and move the needle unit as the second part of the needle sleeve is rotated.

17. The injection device of claim 15, wherein the engaging member is configured to disengage from the needle unit after the second part has been rotated.

18. The injection device of claim 14, further comprising a piston disposed in the cartridge and a piston drive mechanism configured to drive the piston such that when medicament is received in the reservoir the medicament is dispensed via the needle, and wherein the axial movement of the needle sleeve into the housing is adapted to actuate the piston drive mechanism.

19. The injection device of claim 14, wherein the cartridge comprises a medicament in the reservoir.

20. The injection device of claim 1, wherein the housing comprises a proximal end and a distal end, wherein the needle sleeve is provided at the distal end of the housing, and wherein the second part is distal to the first part.

21. The injection device of claim 1, wherein the second part is configured to protrude from the housing prior to actuation of the injection process.

22. The injection device of claim 1, wherein the second part is configured to be pressed against an injection site to actuate the injection process.

23. The injection device of claim 1, wherein the second part is configured to rotate relative to the first part to unlock the locking mechanism so that the needle sleeve is allowed to be moved axially into the housing.

24. An injection device comprising:
a housing having an axis; and
a needle sleeve that is axially movable within the housing, wherein an axial movement of the needle sleeve into the housing is configured to actuate an injection process,
wherein the needle sleeve comprises:
a first part slidably mounted to the housing,
a second part that protrudes from the housing and is rotatably coupled to the first part such that the second part can be rotated relative to the first part about the axis, wherein the second part is configured to be pressed against an injection site to actuate the injection process, and
a locking mechanism configured to prevent the axial movement of the needle sleeve into the housing until the second part of the needle sleeve has been rotated relative to the first part of the needle sleeve.

* * * * *